United States Patent [19]

Ladika et al.

[11] Patent Number: 4,747,840
[45] Date of Patent: May 31, 1988

[54] SELECTIVE PULMONARY ARTERIOGRAPH CATHETER

[76] Inventors: Joseph E. Ladika, 2005 20th St., Ct. West, Bradenton, Fla. 33505; David L. Tempkin, 647 Key Royal Dr., Holmes Beach, Fla. 33510

[21] Appl. No.: 908,327

[22] Filed: Sep. 17, 1986

[51] Int. Cl.$^4$ .............................................. A61M 25/00
[52] U.S. Cl. ..................................... 604/281; 604/280; 604/264
[58] Field of Search .................. 604/280–283, 604/164, 95, 93, 104, 106, 264, 284, 170; 128/341, 343, 772, 656–658

[56] References Cited

U.S. PATENT DOCUMENTS

| | | | |
|---|---|---|---|
| 48,312 | 12/1983 | Farcot | 604/280 |
| 3,503,385 | 3/1970 | Stevens | 604/95 |
| 3,885,561 | 5/1975 | Comi | 604/280 |
| 4,033,331 | 7/1977 | Guss et al. | 604/281 |
| 4,117,836 | 10/1978 | Erikson | 128/658 |
| 4,279,252 | 7/1981 | Martin | 604/280 |
| 4,292,976 | 10/1981 | Banka | 128/658 |
| 4,329,993 | 5/1982 | Lieber et al. | 604/280 |
| 4,547,193 | 10/1985 | Rydell | 604/282 |
| 4,563,181 | 1/1986 | Wijayarathna | 604/280 |

OTHER PUBLICATIONS

Bourassa Cardiovascular Catheters, 1972.
*The New England Journal of Medicine* vol. 262, No. 7, 2/18/60 pp. 325–328.
Catheterization and Cardiovascular Diagnosis, vol. 1, #10, J. H. Grollman, Jr., Editorial: Pigtail Catheters in Pulmonary Angiography; 1984; pp. 390 & 391.

*Primary Examiner*—John D. Yasko
*Assistant Examiner*—Mark F. Colosimo
*Attorney, Agent, or Firm*—Charles J. Prescott

[57] ABSTRACT

An improved catheter for facilitating an antecubital approach to selective cardio-pulmonary arteriography comprising an elongated length of flexible and pliable tubing having a connector at one end. The tubing is preferably open at its distal end and has a tight pigtail contour formed adjacent the distal end and first, second and, optionally, third curved portions arranged in serriatum along the length of the tubing from the pigtail contour, all of which, including the pigtail contour, curve generally in the same direction, and preferably describe a plane. A plurality of spaced apart apertures are provided in an array about the first curved portion for fluid distribution during pulmonary arteriography. The pigtail contour is sized and shaped to pass into the main and branch pulmonary arteries through the right atrium and right ventricle of the heart beginning in the patient's arm. The tube is preferably made of blended polyurethane to enhance torsional rigidity while maintaining pliability and flexibility. A range of sizes are provided within the scope of this invention adaptive to patients with enlarged hearts. The preferred relatively thin tubing size is 5 Fr.

18 Claims, 1 Drawing Sheet

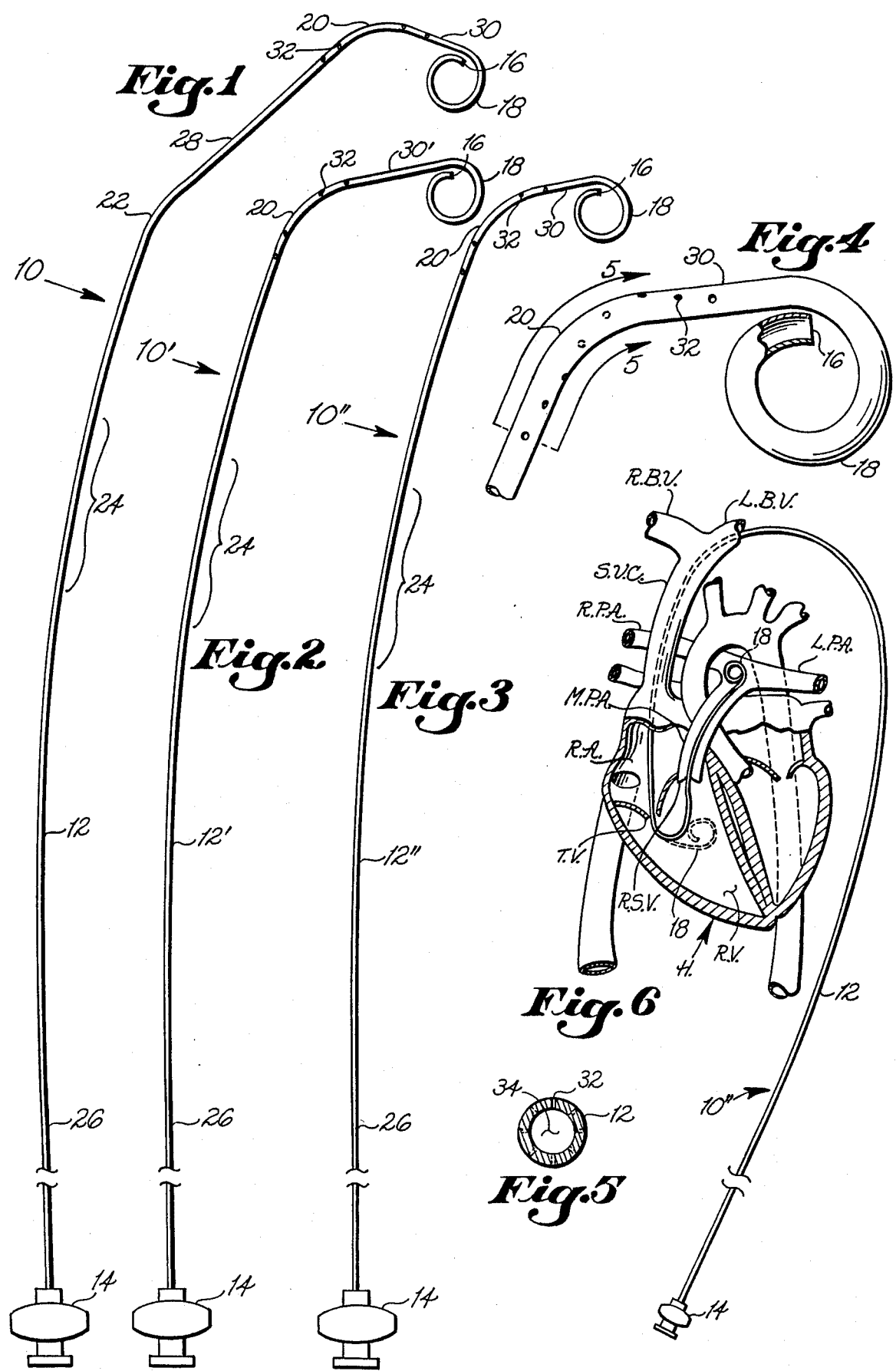

SELECTIVE PULMONARY ARTERIOGRAPH CATHETER

BACKGROUND OF THE INVENTION

This invention relates generally to catheters and more particularly to heart catheters for use in pulmonary arteriography.

Pulmonary catheterization for purposes of arteriography is becoming well known in the field of pulmonary care. In this procedure, generally, a catheter formed of an elongated length of flexible tubing is fed into the patient's body through a vein to the location of interest. Thereafter, a radiopaque liquid is injected and conveyed to the site through the distal end of the catheter during which time x-rays are taken to observe the blood flow and tissue structure therearound.

One aspect of this arteriography is with respect to the main, right, left and secondary pulmonary arteries which connect the right ventricle of the heart and the lungs. The widely accepted technique for pulmonary arteriography (as it is known) is via the femoral approach wherein a catheter if first inserted into the patient's body through a vein in a lower limb and fed through the inferior vena cavae, into the right atrium of the heart, then through the tricuspid valve and into the right ventricle, then through the pulminary semilunar valve and into the main or right or left pulmonary artery. Thereafter, the radiopaque fluid is injected through the catheter for disbursement within the selected portion of the pulmonary artery.

Because of the shape of the heart in relation to the inferior vena cavae, the distal end of the catheter, first moving upwardly into the right atrium, must be then curved slightly downwardly to pass through the tricuspid valve and into the right ventricle, and then must be curved upwardly again to pass through the pulminary semilunar valve. Of no inconsequential risk, to facilitate these necessary gyrations in conjunction with the femoral approach to pulmonary arteriography, in addition to the catheter tubing size required to be larger and more rigid than ideally necessary for the effusion of radiopaque liquid, a rigid guide wire is alternately inserted and removed through portions of the catheter to further enhance the rigidity and shape necessary to effect prior placement and movement of the distal end of the catheter within the pulmonary artery as desired. Further, pulmonary arteriography can, at times, be a lengthy and tedious procedure, and is usually performed on patients who are critically ill. Many times under these circumstances, the heart rhythm is disrupted because of these required strenuous gyrations of the catheter and, in some instances, the interior wall of the heart is bruised and occasionally pierced. A catheter which provides swift placement for selective arteriography with a minimum of complication is therefore desirable.

In an editorial by J. A. Grollman entitled "Pigtail Catheters In Pulmonary Angiography" appearing in *Catheterization and Cardiovascular Diagnosis*, Volume 1, Number 10, Pages 389–391, Dr. Grollman discusses variations of straight catheters which include a pigtail contour at their distal ends. This structure, utilized in conjunction with conventional catheters and applied via the femoral approach is, according to Dr. Grollman, intended to relieve many, if not all, of the above described shortcomings of pulmonary arteriography. Three variations of pigtail catheters are discussed, two of which include pigtail structure at the distal end which is curved in the opposite direction to at least one of the other curvatures formed along the length of the catheter tubing. However, all of these structures there presented are adapted primarily to facilitate the femoral approach to pulmonary arteriography.

A primary advantage in inventing a catheter adapted to be utilized in conjunction with an antecubital approach to pulmonary arteriography is in taking advantage of the geometry between the superior vena cavae, the right atrium and tricuspid valve. Applicants have invented such an improved catheter having a tight pigtail contour formed adjacent its distal end, which invention facilitiates an antecubital approach to pulmonary arteriography and also facilitates the reduction in both diameter and rigidity of the catheter tubing to further reduce the jeopardy into which the patient's heart is placed during such procedures. Additionally, dimensional and contour variations of applicants' invention are provided which are adapted to accommodate patients with enlarged hearts.

BRIEF SUMMARY OF THE INVENTION

This invention is directed to an improved catheter for facilitating an anticubital approach to selective cardiopulmonary arteriography comprising an elongated length of flexible and pliable tubing having a connector at one end. The tubing is preferably open at its opposite distal end and has a tight pigtail contour formed adjacent the distal end and first, second and, optionally, third curved portions arranged in seriatim along the length of the tubing from the pigtail contour, all of which, including the pigtail contour, curve generally in the same direction, and preferably describe a plane. A plurality of spaced apart apertures are provided in an array about the first curved portion for distribution of radiopaque and other fluid during pulmonary arteriography. The pigtail contour is tightly sized and shaped to pass into the main and branch pulmonary arteries through the right atrium and right ventricle of the heart beginning in the patient's arm. The tube is preferrably made of blended polyurethane to enhance torsional rigidity while maintaining pliability and flexibility. A range of sizes are provided adaptive to patients with enlarged hearts. The preferred tubing size is a relatively small 5 Fr.

It is therefore an object of this invention to provide an improved catheter for pulmonary arteriography facilitating an antecubital approach.

It is another object of this invention to provide an improved catheter for pulmonary arteriography which may be reduced in diameter and rigidity to further minimize potential disturbance to a patient's heart tissue and function during catheterization.

It is another object of this invention to provide a range of sizes of an improved catheter for pulmonary arteriography adapted in size and shape to accommodate patients with enlarged hearts.

In accordance with these and other objects which will become apparent hereinafter, the instant invention will now be described with reference to the accompanying drawings in which:

BRIEF DESCRIPTION OF THE DRAWINGS

FIG. 1 is a plan view of one embodiment of the invention adapted for patients with enlarged hearts.

FIG. 2 is a plan view of another embodiment of the invention.

FIG. 3 is a plan view of another embodiment of the invention.

FIG. 4 is an enlarged plan view in partially broken section of the distal end of the invention.

FIG. 5 is a section view in the direction of arrows 5—5 in FIG. 4.

FIG. 6 is a perspective view in partially broken section of a typical patient's heart depicting the invention disposed therein.

DETAILED DESCRIPTION OF THE INVENTION

Referring now to the figures and particularly to FIG. 1, one embodiment of the invention is shown generally at 10 and includes an elongated length of tubing 12 having a connector 14 disposed at one end. The connector 14 is of conventional structure for interconnection to a source of chosen fluids, such as radiopaque liquid and other medications as required during pulmonary arteriography. The tubing 12 is fabricated of a flexible and pliable thin walled material, such as polyurethane. However, a blended polyurethane such as that known as Ducor polyurethane, is preferred because this material maintains the high degree of flexibility and pliability required in a thin walled, small diameter tubing, while providing additional torsional rigidity for manipulation during placement of the catheter within the pulmonary artery.

Referring also to FIG. 4, the distal end 16 of the catheter 10 is, preferrably, open and has formed adjacent thereto a tightly wound pigtail contoured portion 18 which includes a continuous curve through at least about 360 degrees. Adjacent the pigtail 18 is a short first relatively straight portion 30, followed by a first curved portion 20, then a second relatively straight portion 28, followed by a second curved portion 22 blending into a third curved portion 24, and finally a third relatively straight portion 26 ending with the connector 14.

Disposed about the first curved portion 20 as best seen in FIGS. 4 and 5, are a pluralilty of apertures 32 which are disposed in a uniform array equally spaced 3.0 mm. apart about first curved portion 20. These apertures 32, coupled with the open distal end 16, provide the outflow means for the various fluids, including radiopaque fluids, which are to be effused during catheterization. In the preferred embodiment, a total of eight such apertures 32 are provided in an array comprising a spiral evenly disbursed through 360 degrees as best seen in FIG. 5.

Referring now to FIG. 2 and 3, alternate embodiments of the invention are shown generally at 10' and 10''. These embodiments delete the second straight portion 28 from the embodiment 10 of the invention shown in FIG. 1. These embodiments 10' and 10'' are generally useful for heart patients having a relatively normal heart size, whereas the embodiment 10 shown in FIG. 1 is adapted for heart patients with enlarged hearts. The embodiments 10' and 10'' vary one to another only in the length of the first straight portion 30' versus 30. All other aspects of these embodiments 10' and 10', including the pigtail contour 18 and the curved portion 24, are identical to those corresponding segments of the embodiment 10 shown in FIG. 1.

Referring now to FIG. 6, the catheter 10'' is shown disposed within a patient's heart H. The pigtail contour 18 is shown in phantom within the right ventricle R.V. on its way into the main pulmonary artery M.P.A. This invention is particularly useful in conjunction with and truly facilitates, an antecubital approach, as opposed to a femoral approach, to pulmonary arteriography. The primary advantage of the antecubital approach resides in the more favorable physical arrangement of the superior vena cavae S.V.C. with respect to the right atrium and tricuspid valve T.V. In utilizing the ante cubital approach, use of the left arm is preferred by applicants which begins, in sequence, with the patient's cephalic vein, proceeding through the auxiliary vein, the subclavian vein, through the left brachiocephalic vein L.B.V. and into the superior vena cavae S.V.C. Once the pigtail contour has entered the right atrium R.A., it is then passed through the tricuspid valve T.V., into the right ventricle R.V. After the pigtail contour portion 18 is within the right ventricle R.V., it must then be upturned and fed through the pulmonary semilunar valve P.S.V. and into the main pulmonary artery M.P.A. At this point, the positioning of the pigtail 18 and the array of apertures 32 may be selective within the main pulmonary artery M.P.A. or within the right or left pulmonary artery R.P.A., L.P.A., or second order pulmonary arteries. Thereafter, the appropriate fluid, including a radiopaque liquid, is injected through the catheter 10 for x-ray observation of its flow.

To assist in this manipulative process, placement and movement of the catheter 10, 10' or 10'' is assisted by inserting a small diameter (preferrably 0.035 inch diameter) guidewire therethrough, the guidewire either being pushed into or withdrawn from the catheter tubing 12, 12' or 12'' and, at the appropriate point, withdrawn entirely. Additionally, in some instances, manipulation of the pigtail portion into the right and left pulmonary arteries R.P.A. and L.P.A., occasionally requires reinsertion of the guide wire for additional torque control. However, use of Ducor blended polyurethane reduces the necessity for this portion of the procedure. Further, on retraction from the main pulmonary artery M.P.A. into the right atrium R.A., the pigtail 18 may become hooked in the chordae tendineae of the tricuspid valve T.V. wherein the guidewire is typically reinserted to straighten the pigtail 18.

A substantial benefit provided by this invention resides in the reduction in the diameter of the tubing 12, 12' and 12''. This is facilitated by the unique configuration and arrangement of the curved portions and straight portions along the length of the catheters 10, 10' and 10'' which facilitates the antecubital approach. Using the femoral approach, the diameter and rigidity of the tubing in catheters used in this approach have to be larger and more rigid in order to accomplish the manipulation necessary to negotiate the catheter from the inferior vena cavae I.V.C. as previously described. Because the fluid dispersion is easily and effectively otherwise accomplished through thinner catheter tubing 12, 12' and 12'', considerable reduction in the jeopardy to which the critically ill patient's heart is subjected is realized by the physical reduction in size and rigidity of the catheters 10, 10' and 10''. The invention has thus enabled the preferred size or diameter of the tubing 12, 12' and 12'' to be reduced to 5 Fr.

To reiterate, the material used generally in manufacturing the tubing 12 is polyurethane which possesses the necessary physical properties of pliability and flexibility desired. In certain circumstances, because additional torsional rigidity is required, a blended polyurethane material such as distributed and known as Ducor polyurethane is further preferred.

Referring again to FIG. 1, the preferred orientation between first straight portion 30 and second straight portion 28 is generally about 120 degrees one to another. The preferred orientation between the second straight portion 28 and the third straight portion 26 is generally about 130 degrees one to another through curved portion 24. This embodiment 10, having second straight portion 28 is provided to accommodate patient's with enlarged hearts. However, the other embodiments of the invention 10' and 10" as shown in FIGS. 2 and 3 do not include this second straight portion 28 of 10, but rather include an immediate blended transition from the first curved portion 20 into the second curved portion 24. The second curved portion 24 in FIG. 2 and 3 exactly corresponds to the previously referenced curved portion 24 of catheter 10 as referenced in FIG. 1.

In all embodiments of the invention, first curved portion 20 is of a substantially smaller uniform radius than the more gradual and elongated curved portion designated at 24, while all of the curved portions, including the pigtail contour 18 generally curve in a similar direction, and further, define a plane.

While the instant invention is shown and described herein in what is conceived to be the most practical and preferred embodiment, it is recognized that departures may be made therefrom within the scope of this invention, which is therefore not to be limited to the details disclosed herein, but is to be accorded the full scope of the claims so as to embrace any and all equivalent apparatus and articles.

What is claimed is:

1. A cardio-pulmonary arteriography catheter for facilitating an antecubital approach to the pulmonary artery through an enlarged right atrium of the heart and the tricuspid valve comprising:

a length of relatively thin-walled, flexible and pliable tubing having a connector at one end and a distal end;

said tubing having a pigtail contour adjacent said distal end and a first, second and third curved portion arranged seriatim along said tubing from said pigtail contour;

said pigtail contour and said first, second and third curved portions generally curving in a similar direction;

said tubing having a plurality of apertures disposed through said tubing in a spaced array;

said first curved portion spaced from said pigtail contour by a first relatively straight portion of said tubing;

said first and second curved portions spaced apart by a second relatively straight portion of said tubing;

said first relatively straight portion being shorter than said second relatively straight portion;

said first relatively straight portion and second relatively straight portion of said tubing extending distances permitting said pigtail contour, said first curved portion and said second curved portion to be simultaneously positioned within an enlarged right atrium of the heart and being preformed so as to predispose said pigtail contour to pass through the tricuspid valve in response to the application of force at said connector end;

said second portion generally merging into said third curved portion;

said third curved portion spaced from said connector by a third relatively straight portion of said tubing;

said first relatively straight portion and said second relatively straight portion disposed in the range of about 120 degrees one to another;

said second relatively straight portion and said third relatively straight portion being disposed in the range of about 130 degrss one to another;

said third curved portion generally more gradual and elongated than said first and second curved portions;

said pigtail contour relatively tightly structured to pass into a patient's pulmonary artery through the right atrium and the tricuspid valve of the heart;

said connector adapted for connection to a fluid source.

2. A catheter as set forth in claim 1, wherein:
   said tubing distal end is open.

3. A catheter as set forth in claim 2, wherein:
   said first, second and third curved portions are of separate uniform radii.

4. A catheter as set forth in claim 3, wherein:
   said tubing and said first, second and third curved portions and said pigtail contour define a plane.

5. A catheter as set forth in claim 2, wherein:
   said tubing is polyurethane.

6. A catheter as set forth in claim 2, wherein:
   said tubing is blended polyurethane.

7. A catheter as set forth in claim 2, wherein:
   said spaced array of said plurality of apertures is a spiral disposed about said first curved portion.

8. A catheter as set forth in claim 2, wherein:
   said catheter is 5 Fr.

9. A cardio-pulmonary arteriography catheter for facilitating an antecubital approach to the pulmonary artery through the right atrium of the heart and the tricuspid valve comprising:

a length of relatively thin-walled, flexible and pliable tubing having a connector at one end and a distal end;

said tubing having a pigtail contour adjacent said distal end and a first and second curved portion arranged seriatim along said tubing from said pigtail contour;

said pigtail contour and said first and second curved portions generally curved in a similar direction;

said tubing having a plurality of apertures disposed through said tubing in a spaced array;

said first curved portion spaced from said pigtail contour by a first relatively straight portion of said tubing;

said first relatively straight portion of said tubing extending a distance permitting both said pigtail contour and said first curved portion to be simultaneously positioned within the right atrium of the heart and being preformed so as to predispose said pigtail contour to pass through the tricuspid valve in response to the application of force at said connector end;

said first curved portion generally merging into said second curved portion;

said second curved portion spaced from said connector by a second relatively straight portion of said tubing;

said first relatively straight portion being shorter than said second relatively straight portion and being disposed generally in the range of about 100 degrees one to another;

said second curved portion generally more gradual and elongated than said first curved portion;

said pigtail contour relatively tightly structured to pass into a patient's pulmonary artery through the right atrium and the tricuspid valve of the heart;

said connector adapted for connection to a fluid source.

10. A catheter as set forth in claim 9, wherein: said tubing distal end is open.

11. A catheter as set forth in claim 10, wherein: said first and second curved portions are of separate uniform radii.

12. A catheter as set forth in claim 11, wherein: said tubing and said first and second curved portions and said pigtail contour define a plane.

13. A catheter as set forth in claim 10, wherein: said tubing is polyurethane.

14. A catheter as set forth in claim 10, wherein: said tubing is blended polyurethane.

15. A catheter as set forth in claim 10, wherein: said spaced array of said plurality of apertures is a spiral disposed about said first curved portion.

16. A catheter as set forth in claim 10, wherein: said catheter is 5 Fr.

17. A catheter as set forth in claim 1, wherein:
said pigtail contour is a tightly wound continuous curve extending through at least 360 degrees.

18. A catheter as set forth in claim 9, wherein:
said pigtail contour is a tightly wound continuous curve extending through at least 360 degrees.

* * * * *